United States Patent [19]

Roche et al.

[11] Patent Number: 4,563,778
[45] Date of Patent: Jan. 14, 1986

[54] PROSTHETIC ACETABULAR CUP

[75] Inventors: Karen M. Roche, Stillwater; Robert M. Eyerly, White Bear Lake, both of Minn.

[73] Assignee: Minnesota Mining and Manufacturing Company, St. Paul, Minn.

[21] Appl. No.: 469,125

[22] Filed: Feb. 23, 1983

[51] Int. Cl.$^4$ .............................................. A61F 1/00
[52] U.S. Cl. .................... 623/22; 128/92 C; 128/92 CA; 623/16; 623/18
[58] Field of Search .............. 3/1, 1.9, 1.91, 1.911, 3/1.912, 1.913; 128/92 C, 92 CA

[56] References Cited

U.S. PATENT DOCUMENTS

| | | | |
|---|---|---|---|
| 3,698,017 | 10/1972 | Scales et al. | 3/1 |
| 4,285,071 | 8/1981 | Nelson et al. | 3/1.912 |
| 4,437,193 | 3/1984 | Oh | 128/92 C |

FOREIGN PATENT DOCUMENTS

| | | | |
|---|---|---|---|
| 2845231 | 5/1979 | Fed. Rep. of Germany | 3/1.912 |
| 2519454 | 1/1982 | France | 3/1.912 |
| 2080118 | 2/1982 | United Kingdom | |
| 0483980 | 9/1977 | U.S.S.R. | 3/1.912 |

OTHER PUBLICATIONS

Harris, William H. and White, Richard D., Jr., "Socket Fixation Using a Metal-Backed Acetabular Component for Total Hip Replacement", *The Journal of Bone and Joint Surgery, Incorporated*, vol. 64-A, No. 5, Jun. 1982, pp. 745-748.

Vasu, R., Carter, D. R. and Harris, W. H., "Stress Distributions in the Acetabular Region—I. Before and After Total Joint Replacement", *J. Biomechanics*, vol. 15, No. 3, pp. 155-164, 1982.

Carter, Vasu and Harris, "Stress Distributions in the Acetabular Region—II. Effects of Cement Thickness and Metal Backing of the Total Hip Acetabular Component", *J. Biomechanics*, vol. 15, No. 3, pp. 165-170, 1982.

Harris, William H., M.D., "Advances in Total Hip Replacement".

*Primary Examiner*—Richard J. Apley
*Assistant Examiner*—David J. Isabella
*Attorney, Agent, or Firm*—Donald M. Sell; James A. Smith; Robert W. Hoke, II

[57] ABSTRACT

An integral prosthetic acetabular cup assembly and a method for making the same including an inner liner contacting an outer backing and a plurality of spacers mechanically entrapped between the inner liner and the outer backing. The spacers may be made of a material different from that of the inner liner and of the outer backing.

7 Claims, 8 Drawing Figures

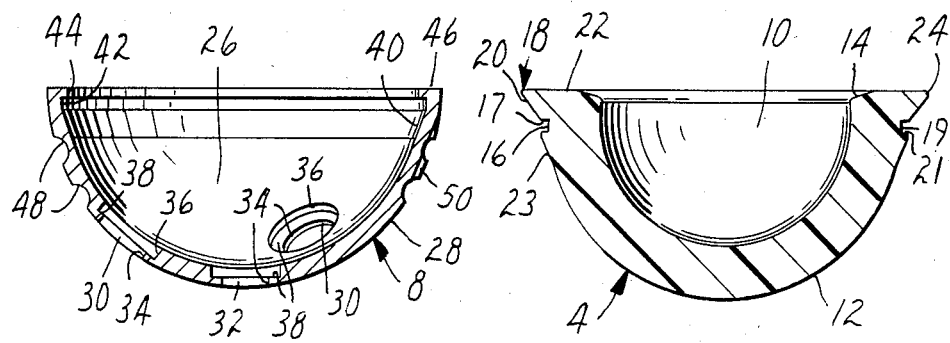
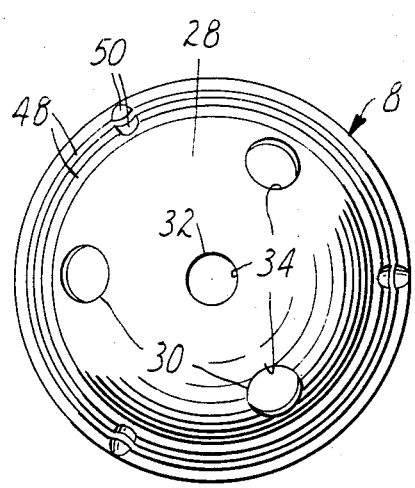
FIG. 4
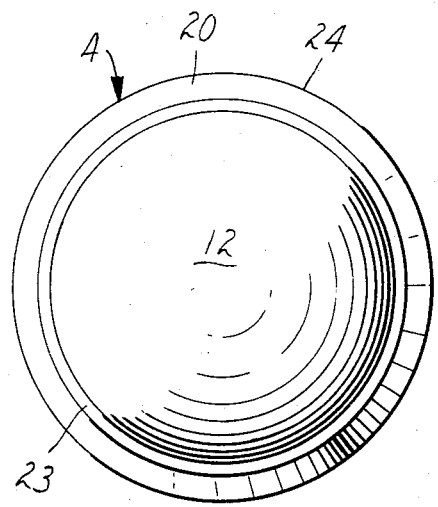
FIG. 6
FIG. 5
FIG. 7
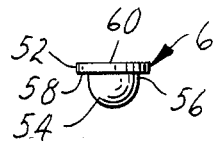
FIG. 8

PROSTHETIC ACETABULAR CUP

The present invention relates to prosthetic acetabular cups. More particularly, it relates to prosthetic acetabular cups for use with a femoral head and neck prosthesis in effecting total hip joint replacements.

Total hip replacement is said to cause changes in the pattern of stress transmission in the acetabular region. After joint replacement, the contact force at the cup surface tends to push the cup into the cancellous bone between the medial and lateral walls of the ilium. As a result, there is an increase in compressive stress in the cancellous bone immediately superior to the cup. In addition, the penetration of the cup into the cancellous bone tends to spread the walls of the ilium and create higher tensile and compressive stresses in the cancellous bone. Simultaneously, significant tensile stresses are created in the inferior portion of the cement layer.

The stresses in the cancellous bone and cement after total hip replacement may relate to eventual loosening of the acetabular component. Acetabular component loosening is said to be the major long term complication in total hip replacement. This has been observed in the form of roentgenographic evidence of demarcation between cement and bone around the acetabular component. Loosening and migration of the acetabular cup may be related to progressive cracking of the cement and the accompanying biological response around the component. High stresses in the bone and/or poor bone quality contribute to these processes.

There have been numerous prior art efforts to diffuse or control the stresses in the cement layer. These efforts include efforts to increase the stiffness of the acetabular cup, efforts to eliminate thin areas of cement which may fragment under heavy load and efforts to eliminate inconsistencies or foreign materials in the cement which may cause localized high stress points.

Acetabular cups molded from a synthetic plastics material such as a high-density polyethylene are well known in the art. It is known to mold such cups with polyethylene spacer pegs or studs to establish a predetermined distance between the back of the cup and the underlying acetabulum. It is also well known in the art to increase the acetabular cup stiffness either by adding additional cement or a metal backing to the cup. This causes a more evenly distributed transfer of the stresses to the walls of the ilium. Increasing the stiffness of the acetabular cup by the addition of a metal backing distributes the stresses over a wider area, reducing peak stresses in the bone and cement. A greater portion of the strong cortical bone at the periphery of the cup bears a higher degree of load than with a relatively flexible acetabular component, and the relatively brittle bone cement is thereby provided with a degree of protection from excessively uneven loading. A metal backing in close contact with a polyethylene liner also limits the cold flow of the polyethylene and reduces the potential for distortion of the polyethylene liner with extended use.

One commercially available acetabular prosthesis has a molded polyethylene liner with a number of molded on polyethylene spacer pegs backed by a titanium alloy shell. It is marketed by Biomet, Inc., Box 587, Airport Industrial Park, Warsaw, Ind. under the unregistered trademark "BIO-CLAD". Although the backing limits the cold flow of the liner, it does not eliminate or even minimize the cold flow. A gap has been found between the liner and the backing. This is believed to form after the molding process as the polyethylene cools. Polyethylene is known to shrink as it cools to room temperature. Also, the molded polyethylene spacers are believed to interrupt the cement layer and cause stress concentrators in a manner to be further explained below.

U.S. Pat. No. 3,698,017 discloses a prosthetic acetabular device of generally hemispherical cup form and including a plurality of annular ribs formed around its outer surface which are said to reduce the possibility of the device being offset within the acetabulum. If the device were offset, the result could be to squeeze away most of the cement over a significant area apart from the groove passing through that area. Hence, through the use of at least three ribs including one adjacent to the rim of the cup, the device is said to provide greater uniformity to the cement layer formed between the cup and the acetabulum. The annular rib configuration, however, is believed to inhibit flow of the soft bone cement around the prosthesis as it is being positioned. Thus, areas closer to the rim of the cup may be left with relatively little cement as the soft cement mass is pushed medially with the introduction of the cup. Additionally, the presence of plastic ribs in the cement layer effectively separates the cement into a series of parallel interconnected discs rather than a more structurally sound hemispherical shape. Also, as noted above, a non-backed cup such as this one subjects the bone cement to non-uniform loading with substantial compressive stresses superiorly.

U.K. Patent Application GB 2080118 A discloses another effort to insure an optimal cement layer thickness between the cup and the acetabulum. It discloses an unbacked acetabular cup having a number of bone cement receiving grooves formed in the external surface of the cup and ungrooved circumferential portions that support integral or inserted studs. The studs are said to act as spacers to facilitate the formation of a layer of bone cement of substantially constant thickness between cup and acetabulum. An integral flange around the circular periphery of the cup serves, in use, to apply pressure to the bone cement to push it into the bone and the grooves of the cup. While the spacers enable the surgeon to control cement thickness, each spacer is a foreign material once pressed within the cement. The presence of any foreign material effectively disrupts the cement mantle.

It is well known that discontinuities in the cement create stress concentrators. The difference in compressive modulus between the stud material and the bone cement disrupts the smooth transfer of loads. Compressive modulus relates to the stiffness or load bearing ability of the material. It may be defined as the ratio of nominal compressive stress in the material at hand to corresponding strain below the proportional limit of the material.

U.S. Pat. No. 3,285,071 discloses a prosthetic cement spacer for controlling the thickness of cement applied between a prosthetic insert and a support member such as an acetabulum. The spacers are described as comprising a generally cylindrical standoff body portion fabricated out of acrylic bone cement of the type normally supplied for surgical use and a pointed wire fabricated out of a steel alloy such as stainless steel. In use, the spacers are individually driven into the acetabular bone surface. The actual use of these individual spacers in an operating room is believed to be troublesome. They are made in different heights and with different wires requiring selection in the operating room. They must be individually driven into the acetabular bone. There is the risk that they may fall over or push out when the bone cement is introduced or when the acetabular cup is adjusted thereon. They require the use of additional instruments and related expertise to properly place them on the acetabular bone surface and to hold them in proper alignment while simultaneously driving them into the underlying bone. If misaligned, initially or during introduction of the bone cement into the acetabulum the thickness of the cement mantle may be adversely affected unbeknownst to the surgeon. The misalignment of a spacer may prevent the proper alignment of the prosthesis within the acetabulum.

The advantage of spacers made of bone cement rather than polyethylene or metal or other materials is said to be their virtual elimination of an interface between the spacers and the bone cement where stresses are known to concentrate. The surface of the polymerized, acrylic bone cement spacers is said to repolymerize when the new acrylic bone cement is introduced, thereby effectively eliminating an interface.

In the case of the spacers disclosed in U.S. Pat. No. 3,285,071 this advantage is not fully realized because of the presence of the pointed wires. The wires, because of their higher modulus, tend to introduce stress concentrations at the interface between the wires and their respective spacers.

SUMMARY OF THE INVENTION

According to the invention there is provided an integral prosthetic acetabular cup including an ultra-high molecular weight polyethylene liner in intimate contact with a suitable metal alloy shell and a plurality of integral standoff or spacer devices. The spacers are mechanically trapped between the liner and the shell to eliminate the need for additional wire-type locating devices, to prevent dislocation of the spacers during surgery and to simultaneously insure equidistant placement of the spacers around the circumference of the shell. The spacers are, preferably, comprised of polymethylmethacrylate, the primary constituent of currently approved bone cement.

Polymethylmethacrylate spacers are said to chemically bond with the bone cement to virtually eliminate an interface between the spacers and the cement. The actual bond may be a chemical and/or mechanical bond formed by solvent cementing, thermal welding, the bone cement shrinking around the spacers or other process. Being of substantially the same material as the bone cement, the compressive modulus of the spacers is virtually the same as that of the bone cement. This relates to a comparably equal load bearing ability between the two materials and eliminates stress concentrators.

By mechanically entrapping the spacers between the liner and the shell, rather than by molding the spacers as part of the liner or the shell, the spacers may develop as bone cements develop over time. Newer bone cements may comprise different materials. As the cements change, so may the spacers change without changing the existing liner or the existing shell. As noted earlier, the materials chosen for the liner and for the shell are chosen because of their bearing qualities, their strength, their stiffness and other factors. Their ability to bond to bone cement may not be a factor.

The materials for spacers, may, preferably, be specifically chosen because of their ability to chemically bond to whatever bone cement is used. Additionally, it is believed that spacers having a compressive modulus similar to that of the bone cement used reduces or eliminates stress concentrators. By making the spacers separate from the liner and from the shell, the materials best suited for each of these items may be utilized. In this way, as the cements change, so may the spacers change to maintain comparable material properties.

An integral, acetabular cup construction utilizing cement-like spacers facilitates operating room procedures. The use of additional instrumentation to place individual spacers on the acetabular bone is eliminated. The risk of human error associated with placing individual spacers on the bone is eliminated, i.e., that the spacers may not be uniformly distributed or the spacers are improperly attached or are attached to degenerated bone material. Also, the need for a multiplicity of separate spacers is eliminated.

With an integral construction, the spacers are securely located on the liner. The spacers may be shaped to allow more universal fitting of the acetabular cup within the acetabulum. By giving the spacers a round or hemispherical shape, greater adjustment or flexibility in the placement of the acetabular cup within the acetabulum is allowed.

Further, as an integral device, the opportunity for misplacement of separate devices has been eliminated. This eliminates another possibility for human error within the operating room.

Perhaps most importantly, the use of an integral acetabular cup construction utilizing mechanically entrapped, cement-like spacers totally eliminates, for the first time, discontinuities and/or interfaces within the cement mantle at which objectionable stress concentrations may appear.

Other objects and advantages of the invention will become more apparent from the following drawings wherein like numerals refer to like parts, the accompanying description and the appended claims.

BRIEF DESCRIPTION OF THE DRAWINGS

FIG. 4 is a sectional view of the metal backing portion of the acetabular cup of FIG. 2.

FIG. 5 is a bottom view of the metal backing of FIG. 4.

FIG. 6 is a sectional view of the inner liner portion of the acetabular cup of FIG. 2.

FIG. 7 is a bottom view of the inner liner of FIG. 6.

FIG. 8 is a side elevational view of the spacers of the acetabular cup of FIG. 2.

DESCRIPTION OF THE PREFERRED EMBODIMENT

Figure 1:
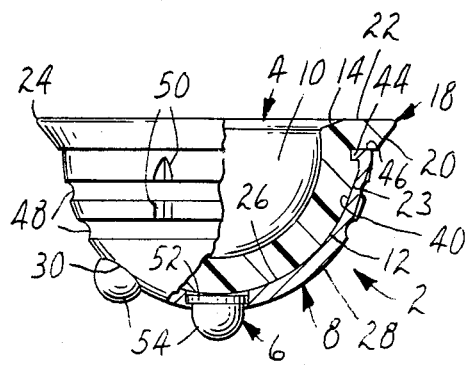
FIG. 1 is a side elevational view of the assembled acetabular cup with portions broken away and portions in section.

Referring to the drawings wherein like reference characters designate like parts throughout the several views, an integral acetabular cup assembly 2 is shown.

Figure 2:
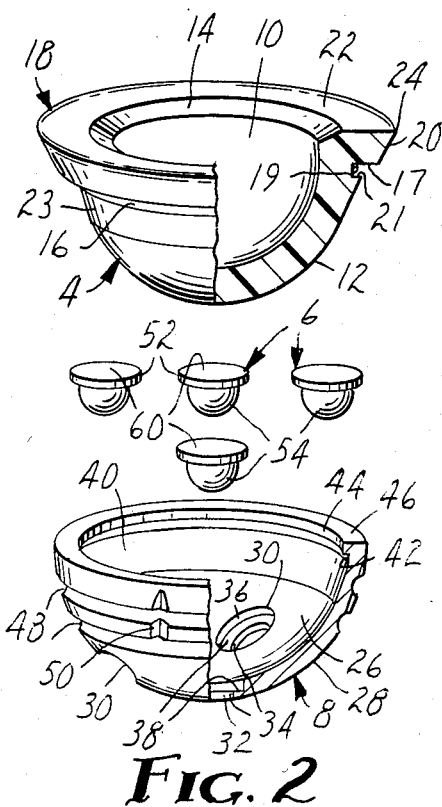
FIG. 2 is an exploded perspective view of the acetabular cup of FIG. 1 with portions broken away and portions in section to illustrate an inner liner, spacers and a metal backing.

As may best be seen in FIG. 2, assembly 2 includes an inner liner 4, a series of spacers 6 and a metal backing 8.

Referring to particular to FIG. 6 and FIG. 7, liner 4 is shown separately in sectional view and bottom view respectively. Liner 4 includes an inner surface 10 and an outer surface 12. Inner surface 10 and outer surface 12 are generally hemispherical in shape. Inner surface 10 terminates at beveled annular surface 14. Outer surface 12 terminates at annular lip 23. Lip 23, in turn, is connected to notch 16 which is comprised of side walls 17, 19 and 21. The surface area between beveled surface 14 and notch 16 comprises an annular, peripheral rim 18. Rim 18 includes a beveled surface 20 connected to sidewall 17 and a top surface 22 connected to beveled surface 14. Surfaces 20 and 22 are connected at radius 24.

In use, inner surface 10 of liner 4 provides the bearing surface for a femoral head used in effecting a total hip replacement. The femoral head and related neck prosthesis used in effecting total hip joint replacement has not been shown as well known in the art. The femoral head which is ultimately chosen for use with liner 4 and the manner in which the femoral head and liner 4 are sized are also well known in the art and form no part of the present invention. Inner liner 4 may be molded or machined from a synthetic plastics material such as a high density polyethylene. An ultra-high molecular weight polyethylene provides proven bearing surface and is generally preferable for receiving the head of the femoral prosthesis. Metal backing 8, on the other hand, may be made of a titanium alloy or other bicompatible metal. The preferred embodiment is machined from titanium-6 alluminum-4 vanadium, ELI grade, bar stock. Such metallic material is commonly used in implants because of its good bio-compatibility, and its relative low modulus of elasticity. The cross-sectional thicknesses of metal backing 8 is generally a uniform 2 millimeters. This is reduced in the area of the grooves as will be explained hereinafter.

Metal backing 8 may be best described in connection with FIG. 4 and FIG. 5. It generally comprises an inner surface 26 and an outer surface 28 with four apertures therebetween labeled 30 and 32. Metal backing 8 is generally hemispherical in shape with aperture 32 at its apex. Apertures 30 are preferably radially disposed from and equidistant from aperture 32.

Apertures 30 and 32 may preferentially be substantially similiar in size and shape. As perhaps best shown in connection with FIG. 4, apertures 30 and 32 are generally cylindrical and counterbored. They include larger cylindrical walls 34, small cylindrical walls 36 and interconnecting wall 38.

Inner surface 26 of metal backing 8 extends radially outward from central aperture 32 to beveled seat 40. Seat 40 is annularly disposed on inner surface 26 and is connected between inner surface 26 and notch 42. The other side of notch 42 is connected to annular lip 44. Notch 42, as well as lip 44, is angularly disposed around the circumference of inner surface 26. Inner surface 26 and outer surface 28 are connected by top surface 46.

Outer surface 28 includes equatorial grooves 48 and polar grooves 50. Equatorial grooves 48 may be best seen in reference to FIG. 2 and FIG. 4. Polar grooves 50, on the other hand, are best seen in FIG. 2 and FIG. 5. The purposes and advantages in grooves 48 and 50 will be described hereinafter.

Referring to FIGS. 2 and 8, the spacers 6 will be described in detail. Spacers 6 are comprised of a generally cylindrically-shaped head portion 52 and a generally hemispherically-shaped body 54. Depending upon the spacer used, they may in addition preferentially include a second cylindrical shank portion 56 to provide additional overall height to the spacers 6. Cylindrical portion 52 is connected to cylindrical portion 56 or hemispherical portion 54 by surface 58. The tops of spacers 6 are comprised of a substantially circular and planar surface 60.

Spacers 6 are preferably made of polymethylmethacrylate as noted earlier. Spacers 6 with an overall height of 3 mm beyond outer surface 28 have been found to be preferred. This is generally considered to be the optimum cement thickness. Any number of spacers 6 may be used in any distribution that will fit a hemisphere. Polymethylmethacrylate bone cement is known to be compatible with all modern prostheses and techniques. The surface of the polymerized acrylic spacers 6 is said to chemically bond when the new cement dough is introduced. This bond is said to eliminate any type of stress riser that may otherwise arise due to the insertion of the spacer within the acetabulum. Hemispherical portion 54 of spacers 6 allows greater flexibility of positioning of acetabular cup assembly 2 within the acetabulum.

Prior to insertion into the acetabulum, inner liner 4, spacer 6 and metal backing 8 must be assembled. First, metal backing 8 is machined from titanium-6 aluminum-4 vanadium, ELI grade bar stock as noted earlier. Next, inner liner 4 is machined from ultra-high molecular weight polyethylene. Spacers 6 are preferably injection molded from polymethylmethacrylate. At room temperature, spacers 6 are dropped into apertures 30 and 32. The outer surfaces of spacers 6 are dimensionally suited and adapted to substantially contact their mating surfaces of apertures 30 and 32. More particularly, walls 34 are juxtapositioned against cyclindrical portions 52, walls 38 contact surfaces 58, and walls 36 are juxtapositioned with surfaces 56.

Next, inner liner 4 is chilled in liquid nitrogen. Being careful not to mar any of the surfaces of inner liner 4, inner liner 4 is placed within metal backing 8. As inner liner 4 warms to room temperature, it expands to a close fit within the metal backing 8. Surfaces 12 and 26 are preferably contacted throughout their interface. This mechanically entraps spacers 6 within their respective apertures 30 and 32, and eliminates the potential for liner 4 to cold flow into any gap that might otherwise exist between surfaces 12 and 26.

Once the assembly is completed and warmed to room temperature, inner liner 4 is mechanically locked within metal backing 8 by the interaction of annular notch 16, annular ridge 23 and annular lip 44. Lip 44 fits snugly within notch 16. Lip 23 is juxtaposed to seat 40 and fits snugly within annular notch 42 to prevent the disassociation of inner liner 4 and backing 8. It has been found that the tolerances on inner liner 4 and metal backing 8 can be closely controlled to achieve the intimate contact required to effectively limit cold flow deformation of the preferred polyethylene liner 4.

Figure 3:
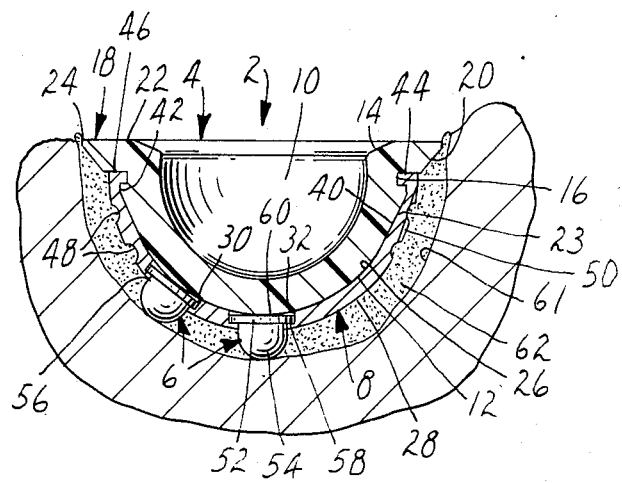
FIG. 3 is a sectional view of the acetabular cup of FIG. 1 cemented to the acetabulum.

The placement of integral acetabular assembly 2 within the acetabulum is shown in FIG. 3. The surgical procedure for inserting assembly 2 within the acetabulum is to prepare the acetabulum by reaming the generally spherical bone surface 61 to a spherical diameter size which is generally equal to the diameter of radius 24 of rim 18. In this manner, the acetabulum will be prepared with an increased size in order to accomodate the additional height or thickness of spacers 6 and yet still position the acetabular cup assembly 2 in the correct position. During this reaming procedure, instruments may be placed in position to check for evenness of reaming and correct alignment. It is important that the acetabulum be cleaned and dried prior to introduction of the acrylic bone cement 62 into the interface.

Care should also be taken not to handle the spacers 6 in order to prevent coating spacers 6 with contaminate materials which could impede the polymerization process. After the acrylic bone cement has been inserted and pressurized on surface 61, acetabular cup assembly 2 is manually pushed into position until it is felt to rest against bone surface 61. At this time, it is possible to firmly hold the acetabular cup in place and simultaneously allow the surgeon to use both hands to smooth and effectively pack the cement around the acetabular cup. Once this packing is completed, the area is trimmed and a smooth surface formed.

When seating assembly 2 within the acetabulum, beveled surface 20 of rim 18 serves to further pressurize the acrylic bone cement 62. The hemispherical portion 54 of spacers 6 further tends to eliminate occlusions in the cement 62 and aid in the placement of assembly 2 upon surface 61 by not being sensitive to positioning. By this it is meant that, regardless of orientation or biasing within the acetabulum, each of spacers 6 will have a substantially identical point contact with surface 61. This insures a uniform thickness to bone cement 62 and further minimizes the possibility of unintentionally forming stress risers within the bone cement.

Equatorial grooves 48 and polar grooves 50 tend to enhance fixation of the prosthesis to the cement layer. Grooves 48 and 50 are generally hemispherical in cross section and preferably radiused at the periphery to avoid stress risers and to insure even and complete filling of grooves 48 and 50 with bone cement 62 when assembly 2 is pressed into the acetabulum. Grooves 48 and 50 are preferably, approximately 1.5 mm deep. Equatorial grooves 48 interlock with bone cement 62 to provide additional stability to assembly 2 during the tension/compresion loading encountered in use. Polar grooves 50 also interlock with cement 62 to provide additional stability to assembly 2. The stability added by grooves 50 is primarily against the torsional forces encountered during use.

From the foregoing, it will be apparent that all of the objectives of this invention have been achieved by the acetabular cup assembly shown and described. It will also be apparent that various modifications and changes may be made by those skilled in the art without departing from the spirit of the invention as expressed in the accompanying claims. Therefore, all matter shown and described is to be interpreted as illustrative and not in a limiting sense.

What is claimed is:

1. An integral, prosthetic acetabular cup assembly comprising:
   a. a plastic inner liner comprising:
      (1) a substantially hemispherically-shaped inner surface adapted to receive a femoral head prosthesis;
      (2) a substantially hemispherically-shaped outer surface; and
      (3) a peripheral rim joining the inner surface with the outer surface;
   b. a metal backing having a plurality of apertures therein comprising:
      (1) a substantially hemispherically-shaped inner surface juxtaposed the outer surface of the liner;
      (2) a substantially hemispherically-shaped outer surface; and
      (3) a peripheral rim joining the inner surface and the outer surface;
   c. a plurality of spacers capable of bonding with a bone cement, each of said spacers having a compressive modulus substantially equal to the compressive modulus of said bone cement and each comprising:
      (1) a body passed through an aperture in the backing; and
      (2) a head joined to the body;
   d. a portion of the periphery of each aperture in the backing formed into a recess dimensioned to receive one of the heads of the spacers whereby the head of each of the spacers is entrapped within one of the recesses when the acetabular cup assembly is assembled; and
   e. means for mechanically locking the liner within the backing.

2. The acetabular cup assembly recited in claim 1 wherein the mechanical locking means comprises:
   a. an annular notch formed on an outer periphery of the outer surface of the inner liner adjacent the liner rim; and
   b. an annular lip connected to the rim of the backing adjacent the inner surface of the backing and disposed within the notch whereby the liner is mechanically locked within the backing.

3. The acetabular cup assembly recited in claim 2 wherein the mechanical locking means further comprises:
   a. an annular notch formed on the outer periphery of the inner surface of the backing between the annular lip and the inner surface of the backing; and
   b. an annular lip connected to the annular notch of the inner liner adjacent the outer surface of the inner liner and disposed within the notch on the backing.

4. The acetabular cup assembly recited in claim 3 wherein the outer surface of the backing has a plurality of annular grooves therein.

5. The acetabular cup assembly recited in claim 4 wherein the outer surface of the backing has a plurality of polar grooves therein equidistantly spaced around the circumference of the outer surface.

6. The method of assembling a prosthetic acetabular cup from an inner liner, a backing comprising an outer surface, an inner surface and a peripheral rim connecting the outer surface to the inner surface and having a plurality of apertures therein connecting the outer surface to the inner surface, and a plurality of spacers each comprising a head connected to a body, comprising the steps of:
   a. passing the bodies of the spacers through the apertures from inside the backing;
   b. contacting the heads of the spacers with the inside of the backing whereby the passage of the bodies of the spacers through the apertures is stopped;
   c. shrinking the inner liner by chilling it significantly below room temperature;
   d. placing the inner liner within the backing and below the peripheral rim of the backing; and
   e. expanding the inner liner by warming it to essentially room temperature thereby locking the inner liner below the peripheral rim of the backing whereby the inner liner and the inner surface of the backing are essentially contacted over substantially the entire interface between the inner liner and the inner surface of the backing thereby entrapping the heads of the spacers between the inner liner and the backing.

7. The acetabular cup assembly recited in claim 5 wherein the inner surface of the backing contacts the outer surface of the liner over substantially the entire interface between the surfaces.

* * * * *